(12) United States Patent
Jung et al.

(10) Patent No.: US 11,298,476 B2
(45) Date of Patent: *Apr. 12, 2022

(54) VIBRATING BLISTER

(71) Applicant: Boehringer Ingelheim International GmbH, Ingelheim am Rhein (DE)

(72) Inventors: Andree Jung, Ingelheim am Rhein (DE); Stephen Terence Dunne, Stowmarket (GB)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 1017 days.

This patent is subject to a terminal disclaimer.

(21) Appl. No.: 15/967,787

(22) Filed: May 1, 2018

(65) Prior Publication Data

US 2018/0243519 A1   Aug. 30, 2018

Related U.S. Application Data

(63) Continuation of application No. 14/035,076, filed on Sep. 24, 2013, now Pat. No. 9,993,601.

(30) Foreign Application Priority Data

Sep. 26, 2012   (EP) ..................... 12006713

(51) Int. Cl.
*A61M 15/00* (2006.01)
*A61M 15/06* (2006.01)

(52) U.S. Cl.
CPC .......... *A61M 15/00* (2013.01); *A61M 15/003* (2014.02); *A61M 15/0005* (2014.02);
(Continued)

(58) Field of Classification Search
CPC .............. A61M 15/00; A61M 15/0001; A61M 15/0008; A61M 15/005; A61M 15/0028;
(Continued)

(56) References Cited

U.S. PATENT DOCUMENTS 3,795,244 A   3/1974   Lax et al.
4,261,354 A   4/1981   Nelson
(Continued)

FOREIGN PATENT DOCUMENTS

EP   1707232 A2   10/2006
WO   2008034504 A2   3/2008

OTHER PUBLICATIONS

Note: all non-U.S. patent documents and all non-patent literature, which are not submitted with this IDS, ere previously submitted to the U.S. PTO in the parent application U.S. Appl. No. 14/035,076 to which a priority claim has been made.
(Continued)

*Primary Examiner* — Michael J Tsai
(74) *Attorney, Agent, or Firm* — Matthew B. Dernier, Esq.

(57) ABSTRACT

Disclosed is an inhaler and a method for using the inhaler for the inhalation of a formulation from a carrier. The carrier contains the formulation in a receptacle and is set oscillating by an air current. An improved or defined delivery and nebulisation of the preferably powdered formulation is made possible by the fact that the carrier is set oscillating in defined manner, the formulation is dispensed through a
(Continued)

cover element having three to five holes and/or the air current flows onto a fin associated with the carrier and flows past at least substantially only one flat side of the carrier.

19 Claims, 5 Drawing Sheets

(52) U.S. Cl.
CPC .... *A61M 15/0028* (2013.01); *A61M 15/0035* (2014.02); *A61M 15/0041* (2014.02); *A61M 15/0043* (2014.02); *A61M 15/0051* (2014.02); *A61M 15/0045* (2013.01); *A61M 15/06* (2013.01); *A61M 2202/064* (2013.01); *F04C 2270/041* (2013.01)

(58) Field of Classification Search
CPC ............ A61M 15/003; A61M 15/0035; A61M 15/0041; A61M 15/0042; A61M 15/06; A61M 2202/06; A61M 2202/064; A61M 15/0005; A61M 15/0006; A61M 15/0031; A61M 15/0033; A61M 15/0045; A61M 15/0046; A61M 15/0048; A61M 15/0086
See application file for complete search history.

(56) References Cited

U.S. PATENT DOCUMENTS

| | | |
|---|---|---|
| 5,239,991 A | 8/1993 | Chawla |
| 5,337,740 A | 8/1994 | Armstrong |
| 5,483,954 A | 1/1996 | Mecikalski |
| 6,286,507 B1 | 9/2001 | Jahnsson |
| 8,528,548 B2 | 9/2013 | Kladders |
| 2004/0057159 A1 | 3/2004 | Kuwajima |
| 2005/0087473 A1 | 4/2005 | Fabricius |
| 2009/0095294 A1 | 4/2009 | Smyth et al. |
| 2009/0223516 A1 | 9/2009 | Connelly |
| 2010/0051023 A1 | 3/2010 | Kladders |
| 2010/0059051 A1 | 3/2010 | Kladders |
| 2012/0234322 A1 | 9/2012 | Smyth |
| 2013/0042864 A1* | 2/2013 | Adler ................ A61M 15/0008 128/203.15 |

OTHER PUBLICATIONS

International Search Report for PCT/EP2013/069780, 3 pages, dated Jun. 11, 2013.

* cited by examiner

VIBRATING BLISTER

CROSS REFERENCE TO RELATED APPLICATIONS

This application is a continuation of U.S. Ser. No. 14/035,076, filed Sep. 24, 2013, which claims the benefit of EP 12006713, filed Sep. 26, 2012, the entire disclosures of which are hereby incorporated by reference.

FIELD OF THE INVENTION

The present invention relates to an inhaler for the inhalation of a formulation from a carrier that is preferably in the form of a belt, strip, blister and/or film, wherein the carrier is set oscillating by the impact of an air current. The invention also relates to the delivery and nebulisation of a formulation from such an inhaler.

BACKGROUND OF THE INVENTION

Figure 3:
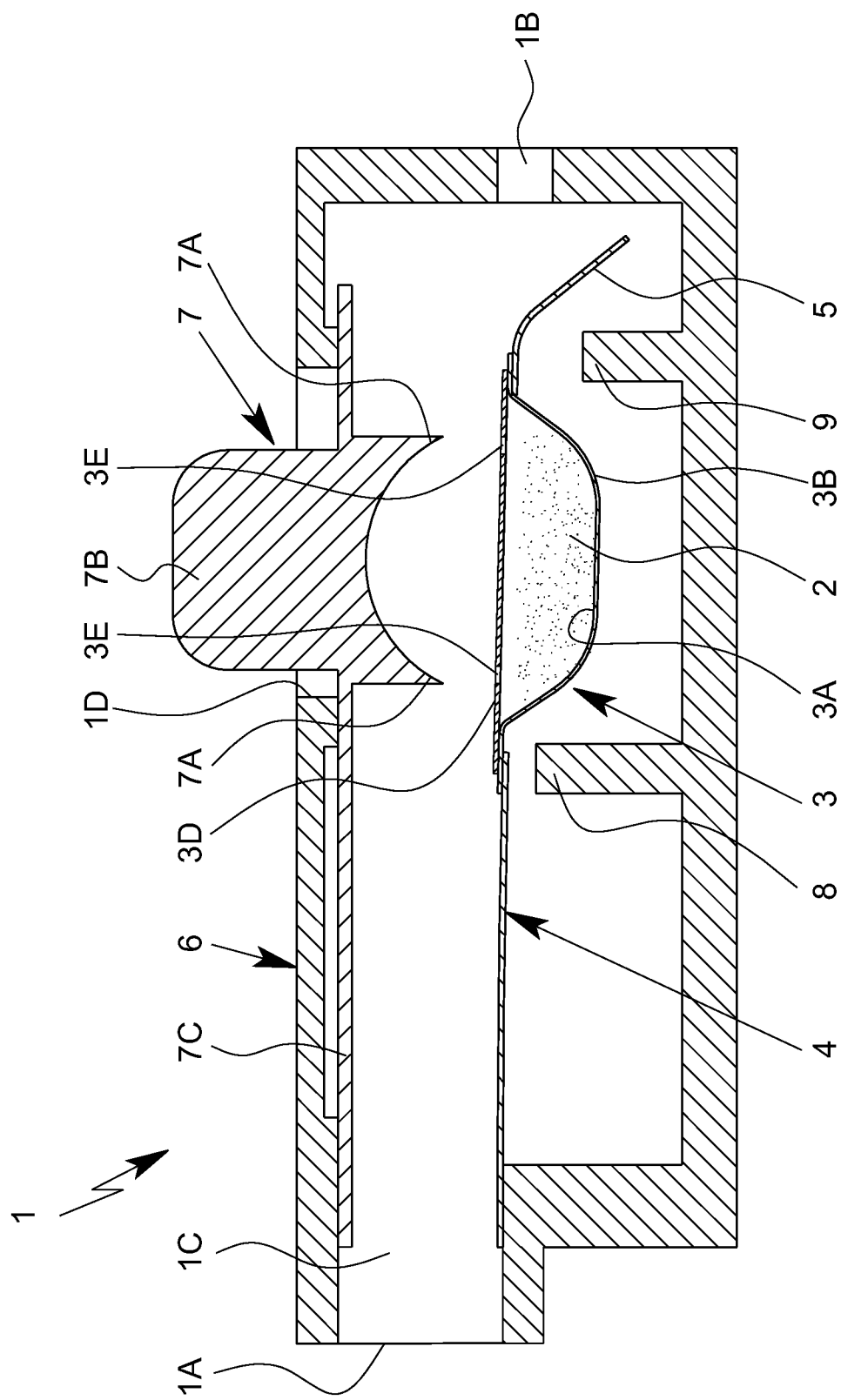
Figure 4:
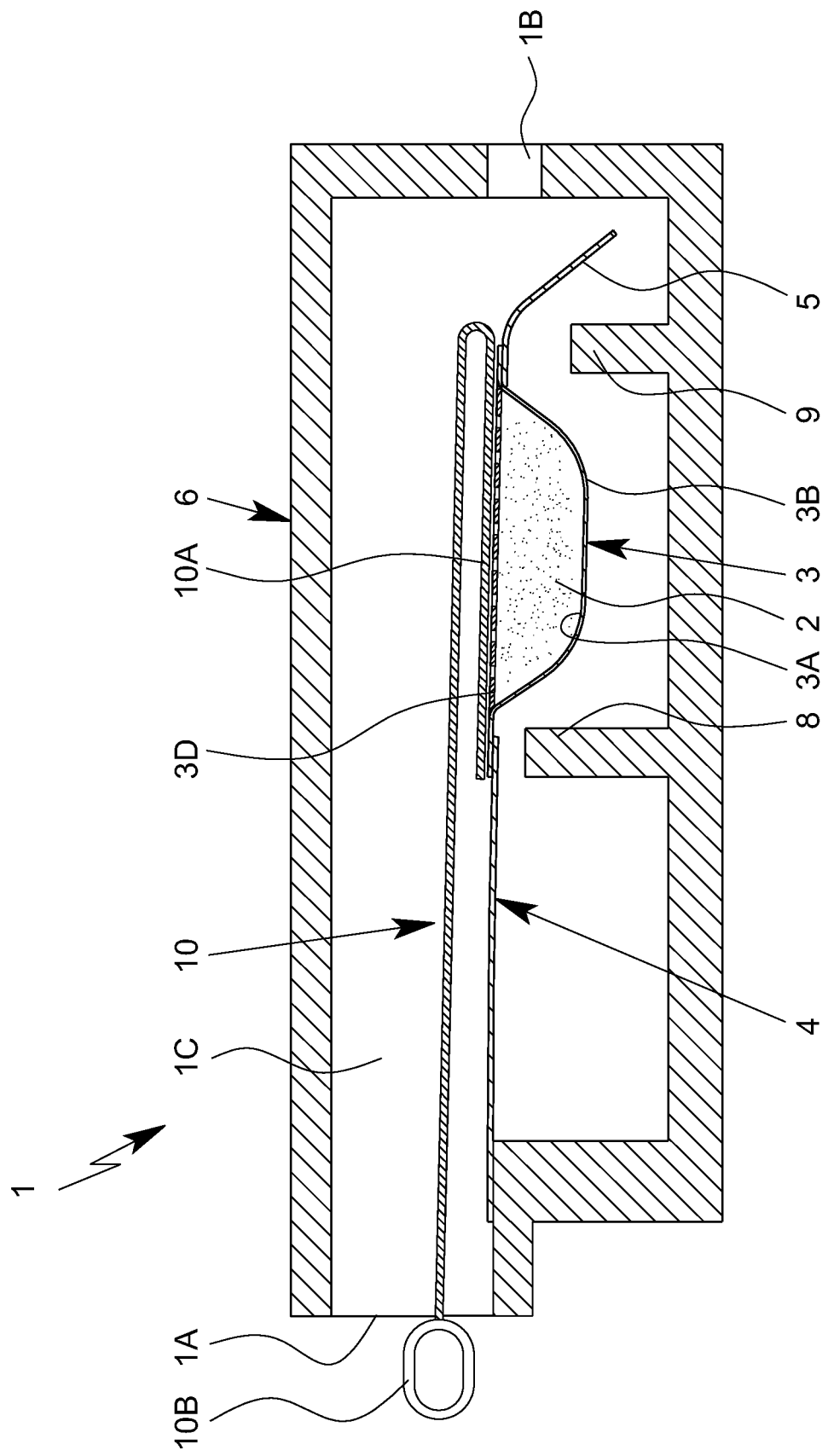

WO 2008/034504 A2, which forms the starting point for the present invention, discloses an inhaler for inhaling a formulation from a carrier, wherein, for the purposes of, or during, the delivery and/or dispersal of the formulation, at least a part of the carrier is set oscillating by an air current. The carrier is, in particular, of a flat, blister-type or film-like construction. FIG. 3 of WO 2008/034504 A2 shows an embodiment in which the carrier is moved or set oscillating directly by the air current. A problem here is that the air current impacts the carrier at right angles to its flat side and the carrier flutters freely.

The present invention is based on the problem of providing an improved inhaler and an improved method, so as to allow effective delivery and in particular nebulisation of an in particular powdered formulation to be achieved in a simple manner and/or to enable a simple and/or inexpensive construction, particularly in the form of a disposable inhaler.

The above problem is solved by an inhaler of the invention or a method of using the inhaler as described herein.

SUMMARY OF THE INVENTION

The present invention relates in particular to an inhaler for the delivery or inhalation of a preferably powdered formulation, i.e., a powder inhaler. However, the formulation may theoretically also be present in liquid phase, as a dispersion or in another fluid is able form.

The formulation is, more particularly, a therapeutic agent or medicament. In particular, the formulation accordingly contains or consists of at least one active substance. The formulation is thus used in particular for medicinal treatment or other therapeutic purposes.

In the present invention, the formulation is held in or by a carrier, particularly pre-metered in individual doses.

According to the proposal, the inhaler comprises a carrier that can be moved or set oscillating, in particular, directly by an air current. Particularly preferably, the carrier comprises a receptacle containing the formulation. Alternatively the carrier may also comprise a plurality of receptacles, preferably, two, in particular containing different formulations.

The carrier is preferably movably held by means of a spring portion. The carrier is preferably directly movable, particularly adapted to be set oscillating, by an air current for delivering and/or dispersing the formulation(s).

According to one aspect of the present invention, the carrier can be set oscillating, or oscillates, in defined manner, particularly with a defined movement, with a defined amplitude and/or with a defined frequency. This contributes to an improved and defined delivery and nebulisation or dispersion.

Preferably, the term "defined movement" denotes a movement that has only certain or specified degrees of freedom. Particularly preferably, the carrier is at least substantially rotatable only about a specified axis, or an axis formed by the spring portion, or only movable in the form of a pivoting movement, the path of movement of the carrier being located in particular in one plane, and a main plane of extent of the flat carrier extending at least substantially always perpendicular to this plane of movement.

The term "defined amplitude" preferably denotes a limitation to the movement or amplitude of the carrier, while if required a limitation may be provided on one side only, i.e., acting only in one direction of movement, for example, in the form of a stop.

The term "defined frequency" preferably denotes a restricted frequency or frequency range at which the carrier oscillates during use. As different air flows may be produced during use, particularly when the air current is generated by the user breathing in, the specified frequency range of the oscillation should preferably be understood as a function of a specified flow rate or a specified flow rate range.

The carrier or spring portion is preferably fixed or held on one side only, more particularly clamped or attached. The carrier or spring portion ends freely on the other side or in such a way that the other side is able to oscillate (freely).

In another aspect of the present invention, the spring portion holds the carrier so as to be preferably movable at right-angles to the air current but at least substantially torsionally rigid in the direction of the air flow. This contributes to a defined movement, amplitude and/or frequency of the carrier.

According to another aspect of the present invention the spring portion preferably comprises two parallel extending spring bars and/or an opening, particularly an oblong slot. This contributes to a defined movement, amplitude and/or frequency of the carrier.

According to another aspect of the present invention the carrier can be impacted by the air current at least substantially exclusively from a free end or an opposite end to the spring portion. This helps to ensure the optimum delivery of the formulation, particularly as unnecessary turbulence in the inhaler can be avoided or minimised. Alternatively or additionally, this contributes to a defined oscillation of the carrier.

According to another aspect of the present invention an oblique fin that can be impacted by the air current is preferably associated with the carrier. Particularly preferably, the fin is mounted on a free end of the carrier and/or adjacent to an air inlet of the inhaler. This permits a compact construction and a defined air current onto the carrier and/or an efficient action on the carrier in order to set it oscillating.

According to another aspect of the present invention the carrier or a covering of the carrier is preferably at least partially covered by a covering device which can be manually opened or removed in order to open the carrier or cover for subsequent delivery of the formulation. Particularly preferably, the covering device is opened or removed by pulling a grip element or cover element of the covering device. In this way, perforations, openings or holes previously provided in the cover can particularly preferably be exposed. This contributes to a defined delivery and nebulisation of the formulation.

According to the proposal, the formulation may be delivered, dispersed and/or expelled particularly effectively, in particular, from a corresponding receptacle in the carrier.

The formulation may be delivered using the air current for moving the carrier or a different air current, as desired.

In the present invention, the terms "air" and "air current" are preferably to be understood more broadly as encompassing some other gas or a current of another gas. However, the term "air" will be used consistently hereinafter, as air is normally used as the gas for driving or moving the carrier and/or as a conveying medium for conveying the formulation after its release from the carrier or for dispersing the formulation. Preferably, the air current is generated during inhalation or by breathing in. This is therefore a passive inhaler, in particular.

Particularly preferably, the inhaler is configured for the delivery or administration or inhalation of only a single dose. Particularly preferably, it is thus a disposable device. However, the inhaler may alternatively be designed for multiple use and/or for separately delivering a number of doses of the formulation. For example, a plurality of receptacles are then provided, which can be opened independently of one another.

The above-mentioned aspects and the aspects arising from the remainder of the description and the claims may also be implemented independently of one another, but also in any desired combination.

BRIEF DESCRIPTION OF THE FIGURES

Individual aspects, features, properties and advantages of the present invention will become apparent from the following description of embodiments by reference to the drawings, wherein:

FIG. 1 is a schematic section through a proposed inhaler according to a first embodiment;

FIG. 2 is a schematic horizontal section through the inhaler according to FIG. 1 along the line II-II;

FIG. 3 is a schematic section through a proposed inhaler according to a second embodiment;

FIG. 4 is a schematic section through a proposed inhaler according to a third embodiment with the cover over a receptacle of a carrier closed; and FIG. 5 is a schematic section through the inhaler according to FIG. 4 with the cover open.

In the Figures, the same reference numerals are used for identical or similar parts, even though there is no repetition of the description. In particular, the same or corresponding advantages and properties are obtained. The individual Figures are not drawn to scale, for reasons of representation or simplicity and are reduced to significant components that are relevant to the invention.

DETAILED DESCRIPTION OF THE INVENTION

FIG. 1 schematically shows the structure of a proposed inhaler 1 according to a first embodiment. The inhaler 1 is preferably configured to be portable and/or operates, in particular, purely mechanically.

The inhaler 1 serves for the delivery or inhalation of a preferably powdered formulation 2 in the sense mentioned hereinbefore. The formulation 2 is preferably pre-metered in a single dose or a plurality of doses.

In the embodiment shown, the formulation 2 is preferably pre-metered, i.e., pre-metered beforehand outside the inhaler 1 in a single dose or a plurality of doses. However, it is also theoretically possible not to meter the formulation 2 until immediately before inhalation and/or in the inhaler 1.

A carrier 3 carries the formulation 2 or holds it in readiness. In particular, the carrier 3 comprises at least one recess or receptacle 3A or the like for holding, in particular, a dose of the formulation 2. However, other design solutions are also possible here. For example, the formulation 2 may be arranged or distributed over the surface or in an area of the surface or over the entire surface of the carrier 3.

The carrier 3 is particularly of flexible, flat, belt-shaped, strip-shaped, blister-type and/or film-type construction. It is made of or produced from a suitable material, particularly plastics, metal foil, a composite material or the like.

The carrier 3 may have only one receptacle 3A or a plurality of receptacles 3A. Each receptacle 3A may be covered, if required, with an optional cover 3D, as shown by way of example in FIG. 1. For expelling the formulation 2, the cover 3D can preferably then be opened, pulled off or the like. For example, the cover 3D may be cut open, torn open, perforated or in some other way at least partially removed and/or opened, to enable the formulation 2 to be expelled. Particularly preferably, the opening is done by an associated opening device 7, optionally not until the carrier 3 is moved. The opening device will be discussed in more detail hereinafter.

The cover 3D and/or one or more relatively small outlet openings, apertures or holes 3E (cf. FIG. 5) or the like particularly preferably cause the formulation 2 to be released and expelled relatively slowly—particularly at a desired rate.

As schematically shown in FIG. 1, the carrier 3 is preferably of a blister-type construction. In particular, the carrier 3 comprises a carrier element or base element 3B which particularly comprises a recess or is thermoformed in order to form the receptacle 3A or a holding chamber for the formulation 2. The holding chamber or receptacle 3A is preferably covered by the cover 3D.

In particular, the carrier element or base element 3B is formed by a film or a film material or composite material.

The cover 3D is preferably sealed or laminated onto the carrier element or base element 3B.

Particularly preferably, the cover 3D is formed by a thin film, for example, of plastics, aluminium, a composite material or the like.

Particularly preferably, the carrier 3 or its carrier element/base element 3B and cover 3D form a blister or a blister pack.

In the embodiment shown the inhaler 1 is preferably embodied as a single-use inhaler and/or for dispensing or administering only one dose. However, it may theoretically also be a multi-channel inhaler which is preferably designed for independently dispensing several doses of the formulation or different formulations.

If the inhaler is embodied as a multi-channel inhaler the carrier 3 may comprise a plurality of independently openable receptacles 3A and/or finger-like projections each having a receptacle 3A. The different receptacles 3A or finger regions may be connected to one another particularly in an end region or may be connected in such a way that the finger regions or receptacles 3A can be set oscillating independently of one another. The carrier 3 is then movable, for example, at right-angles to the direction of flow and/or the direction of oscillation or can be pulled by the inhaler 1, particularly in order to switch from one receptacle 3A to the next receptacle 3A or in order to bring the next finger region into a position enabling the proposed oscillation and expulsion of the respective dose from the particular receptacle 3A.

The inhaler 1 preferably comprises at least one carrier 3 or is configured to accommodate at least one carrier 3.

As already mentioned, the carrier 3 may also comprise a plurality of receptacles 3A for a plurality of doses, possibly doses of different formulations 2. Thus it is possible, for example, to expel two different formations 2, held in different receptacles 3A, jointly using the air current L and optionally mix them and/or supply them to a patient on inhalation at least simultaneously or possibly sequentially, one after another.

In the embodiment shown, the carrier 3 is preferably fixedly held or arranged in the inhaler 1 and/or is not exchangeable. The inhaler 1 therefore preferably comprises a carrier 3 in the embodiment shown.

The carrier 3 is preferably movably held by means of a spring portion 4. In particular, the carrier 3 is held by the spring portion to be movable at least substantially at right-angles or perpendicularly to its surface extent. Particularly preferably, the spring portion 4 is deformable by spring resilience in order to oscillate the carrier 3. Alternatively or additionally, the carrier 3 may also be configured to be deformable by spring resilience.

Figure 1:
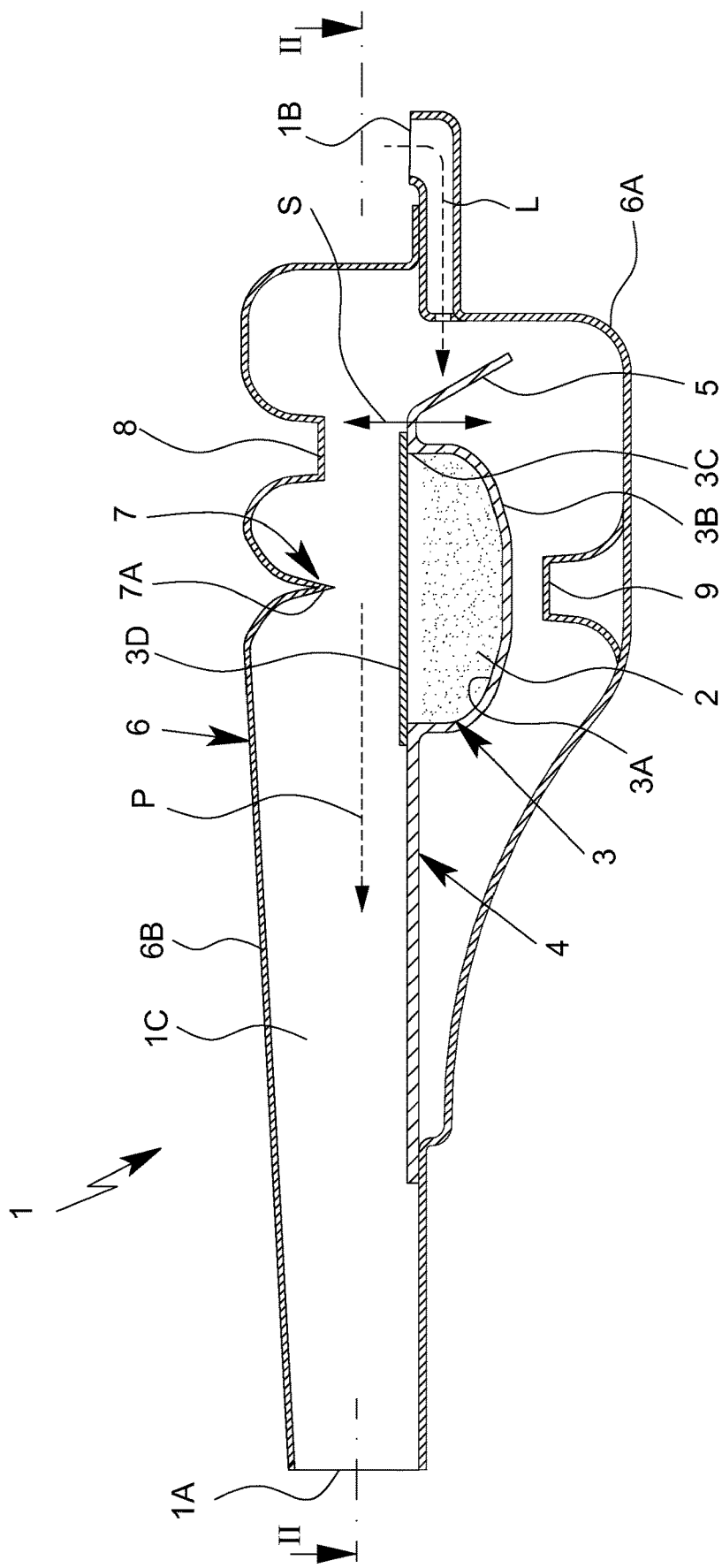

The carrier 3 or its carrier element or base element 3B is preferably at least substantially flat in configuration or is characterised by a main surface extent (in the representation shown in FIG. 1, horizontal and perpendicular to the plane of the drawing, or by a plane parallel to the plane of section II-II of FIG. 1).

The spring portion 4 preferably extends at least substantially in the main plane of extent of the carrier 3 or in a plane parallel thereto.

Particularly preferably, the spring portion 4 forms a (virtual) axis A (cf. FIG. 2), about which the carrier 3 can move, particularly by rotation. At the same time the carrier 3 is guided or held by the spring portion 4. The axis A is not fixed but may vary or migrate in particular in the plane of the spring portion 4 (particularly depending on the material and form of the spring portion 4) and/or may move by translation in other planes. The spring portion 4 in particular is embodied, especially because of the preferred structure, such that the axis A does not tilt but only moves in parallel manner.

The spring portion 4 is preferably at least substantially in bar or leaf form. The spring portion 4 is preferably at least substantially in strip and/or film form.

Figure 2:
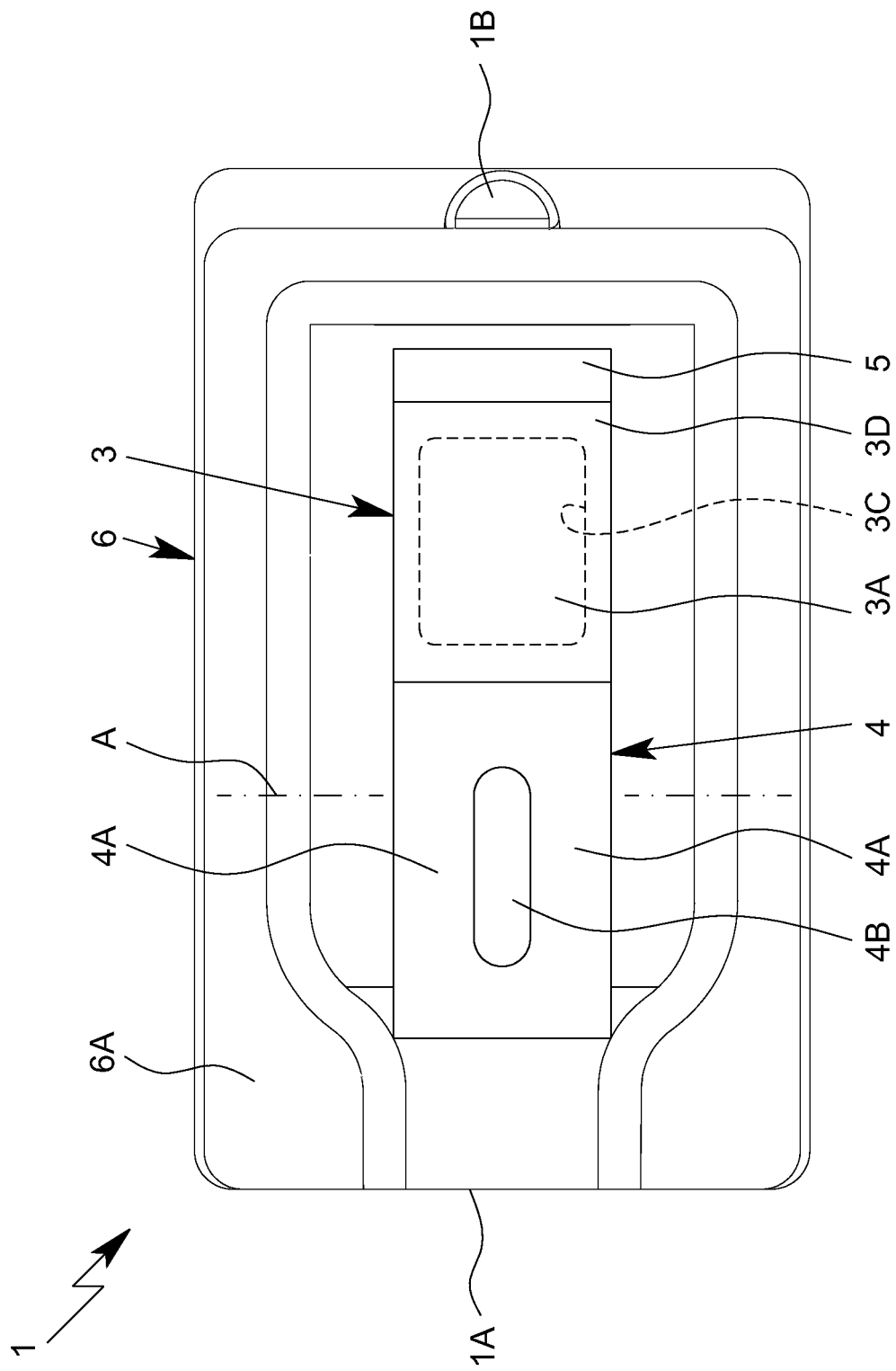

It can be seen from the horizontal section according to FIG. 2 that the spring portion 4 preferably comprises two spring regions or bars 4A and/or at least one opening, preferably a slot or longitudinal slot 4B arranged in particular between them. Tests have shown that highly defined spring and torsional characteristics can be achieved in this way. This greatly contributes to a defined delivery of the formulation 2 and a defined movement, amplitude and/or frequency of the carrier 3.

Moreover, the opening prevents the spring portion 4 and carrier 3 from being able to close off the flow path like a valve when an end position is reached. Rather, air can then continue to flow through the opening.

Preferably, the size of the opening is at least 10%, particularly about 20% or more of the total area of the spring portion 4 and/or less than 70%, particularly preferably less than 50% of the total area of the spring portion 4.

In the embodiment shown, the opening is preferably in the form of a slot. However the opening may also be of a different shape.

Moreover, a number of openings may also be provided.

The spring portion 4 may be formed by a separate piece of material or, as indicated in the first embodiment, may be formed by the carrier element or base element 3B of the carrier 3.

The spring portion 4 may be formed in one piece with the carrier 3 and/or may be made from the same material. For improved elasticity, the material in the region of the spring portion 4 may, for example, also be of thinner construction and/or it may be drawn out. Alternatively or additionally, the elasticity of the spring portion 4 may also be influenced or determined by a corresponding arrangement and/or size of the opening 3.

Alternatively or additionally, the spring portion 4, preferably of the leaf type, may also be made from a different material, for example, a resilient plastics material, particularly polycarbonate, or from metallic spring steel sheet.

The carrier 3 is preferably attached to the spring portion 4 by adhesion or welding, but the use of moulding or overmoulding to form the connection is also possible. In general terms, the attachment may be made by any suitable method.

In the embodiment shown, the spring portion 4 is preferably fixedly mounted or secured at one end to the inhaler 1 or a housing 6 of the inhaler 1, preferably by adhesive bonding, welding, clamping or the like. Adjoining the other or free end of the spring portion 4 is preferably the carrier 3—particularly as an extension thereof.

Particularly preferably, a fin 5 is associated with the carrier 3, as shown in FIGS. 1 and 2. The fin 5 is preferably mounted on free end of the carrier 3 or the end that is remote from the spring portion 4.

The fin 5 preferably slopes to the surface extent of the carrier 3 and/or the direction of the incoming air current L. The slope of the fin 5 to the surface extent of the carrier 3 or to the air current is preferably at least substantially 30° to 70°, particularly substantially 40° to 50°, most preferably substantially 45°.

The fin 5 is preferably formed in one piece with the carrier 3 or formed by the (same) carrier material, particularly by corresponding shaping.

Alternatively, the fin 5 may also be made from another material or piece of material, for example, a spring steel sheet, which is attached to the carrier 3.

Preferably, a soft or rounded transition, particularly with a radius of at least 1 to 2 mm is provided between the carrier 3 and the fin 5.

The fin 5 is preferably arranged as close as possible to the receptacle 3A, i.e., in particular immediately adjacent thereto.

The carrier 3 can be moved, more particularly set oscillating, by the air current L for expelling the formulation 2—i.e., for releasing the formulation 2 from the carrier 3 or from the receptacle 3A. The air current L may act on or move the carrier 3 directly or indirectly.

For oscillating the carrier 3, the spring portion 4 is preferably deformed by spring resilience. In particular, the spring portion 4 also oscillates.

Preferably, the air current L also forms a delivery medium for dispersing and/or conveying the formulation 2 that has been released by the carrier 3 particularly as a result of the movement of the latter, and preferably for expelling the formulation through a mouthpiece or an outlet 1A of the inhaler 1 and delivering it to a user (not shown). However, a different or separate air current or other air in the sense mentioned previously—i.e., a different gas—may also be used as the delivery medium for the formulation 2.

In the embodiment shown the air current L is preferably produced by the inhalation or breathing in of the user (not shown), particularly by the intake of ambient air.

The air current L sucked in or flowing into the inhaler 1 or its housing 6 through the inlet 1B first strikes the oblique fin 5. The optional fin 5 can assist or bring about the preferred transverse movement or oscillation S of the carrier 3 caused by the air current L.

The carrier 3 is deflected by the air current L and is set oscillating. The plane of movement preferably extends in the plane of the drawing, in the representation provided by FIG. 1. In particular, the carrier 3 performs a rotary or pivoting movement, guided by the spring portion 4 or about the axis A (FIG. 2).

For opening the receptacle 3A or cover 3D the inhaler 1 preferably comprises the opening device 7. The opening device 7 is particularly configured for piercing the cover 3D. For this purpose the opening device 7 preferably comprises at least one piercing element 7A.

In the first embodiment the opening device 7 or the piercing element 7A is preferably formed by a wall area of the inhaler 1 or of the housing 6 of the inhaler 1, particularly an upper part 6B of the housing 6, or is arranged thereon.

Preferably, the opening device 7 or the piercing element 7A or the wall area can be pressed in manually, so that the cover element 7A can pierce the cover 3D, this piercing being carried out, for example, in the starting or central position of the carrier 3 shown in FIG. 1, for example, and/or if the carrier 3 is deflected, in an end position, for example, in which the carrier 3 or its base element 3B abuts on an opposing step 9, for example.

However, it is also alternatively possible for the receptacle 3A or cover 3D to be opened solely by the movement or oscillation of the carrier 3. In this case the wall area does not have to be of flexible configuration. Instead, the opening device 7 or its piercing element 7A is preferably arranged so that piercing takes place automatically when the carrier 3 oscillates accordingly.

After the opening of the receptacle 3A or the cover 3D, as the carrier 3 continues to oscillate, the formulation 2 is expelled by the movement and/or by the air current L. Depending on the opening of the cover 3D, the air current L may also flow through the receptacle 3A in order to deliver the formulation 2.

The air current L carries the powder with it, so as to form a powder-laden air current P, as schematically shown in FIG. 1.

The air current L or powder-laden air current P preferably flows at least substantially exclusively past or along a flat side, in this case the upper flat side or covering side of the carrier 3 or the flat side of the carrier 3 that releases the formulation 2.

The powder-laden air current P may preferably flow at least substantially in a straight line to the outlet 1A of the inhaler 1 and through this it may be delivered to a user (not shown).

The housing 6 of the inhaler 1 in the embodiment shown is preferably made up of the lower part 6A and the upper part 6B or two halves or sections. Particularly preferably, the housing 6 is formed in two parts or two shells or from two half-shells. The two parts or the lower part 6A and the upper part 6B are preferably snap-fitted, glued, welded and/or otherwise attached to one another. Alternatively, the housing 6 or these parts 6A, 6B may also be made in one piece or formed by a collapsible part that is particularly preferably produced by a plastics injection moulding process. However, other design solutions are also possible.

The inhaler 1, the housing 6 and/or the carrier 3 or the receptacle 3A is or are preferably—at least partially—transparent in construction. Thus, a user can very easily tell whether the inhaler 1 has already been used or emptied or is still available for use.

Particularly preferably, the inhaler 1 comprises a mouthpiece which is preferably formed, in the embodiment shown, by the housing 6 and/or in the region of the outlet 1A. Accordingly, the user (not shown) can preferably place the inhaler 1 directly in his or her mouth and breathe in, in order to suck in ambient air and produce the air current L.

The inhaler 1 is preferably configured such that a fall in pressure of about 3 to 5 kPa, particularly preferably of approximately 4 kPa, is obtained at an air current L of 70 l/min.

The inhaler 1 is preferably designed for a flow rate of about 20 to 100 l/min.

The inhaler 1 is preferably configured such that the frequency of the oscillation is at least substantially 50 to 100 Hz, particularly preferably 60 to 90 Hz and most particularly preferably substantially 70 to 80 Hz, particularly at a flow rate of 20 to 100 l/min, particularly preferably at a flow rate of substantially 70 l/min.

The frequency of the oscillation depends particularly on the amount or weight of the filling. In particular, the fill amount in the receptacle 3A is selected so as to achieve a desired frequency. Starting from a specific dose or quantity of active substance, an additional substance or a greater proportion of a particular substance may be added to the formulation, for example, to increase the weight, so as to influence the frequency.

The inhaler is preferably configured such that the amplitude of the oscillation is at least 1 mm, particularly substantially 2 mm and/or less than 10 mm, preferably less than 6 mm, particularly less than 4 mm.

The inlet 1B for the air or the air current L is preferably arranged on the side opposite the outlet 1A and/or adjacent to the free end of the carrier 3 or to the fin 5.

In particular, the direction of the air current L flowing in through the inlet 1B as it strikes the carrier 3 or fin 5 is at least substantially parallel to the main direction of flow of the powder-laden air current P or to the main direction of exit or main delivery direction of the inhaler 1, i.e., at least substantially horizontal in the representation shown in FIG. 1.

The air inlet 1B is preferably formed between or by the two housing parts 6A and 6B.

The inhaler 1 or its housing 6 preferably forms a flow chamber 1C which runs, at least substantially free from steps and/or in a straight line, from the carrier 3 or its receptacle 3A to the outlet 1A, while the cross-section of the flow chamber 1C may decrease, particularly towards the outlet 1A, parallel to the main direction of extent or surface extent of the carrier 3 in the embodiment shown, as shown in FIG. 2, in order to form a mouthpiece or mouthpiece region on the outlet side. However, other design solutions are also possible.

Particularly preferably, the carrier 3 is subjected to air current at least substantially only in the region of its free end and/or only on a flat side.

In order to limit the oscillation S of the carrier 3, the inhaler 1 preferably comprises at least one stop, in this particular embodiment two or more stops 8 and 9, as shown in FIG. 1.

In the embodiment shown the stops 8 and 9 are preferably formed by the housing 6 or its wall. However, other design solutions are also possible.

The stops 8 and 9 limit the amplitude or deflection of the carrier 3 during oscillation. This contributes to a defined oscillation and hence to a defined delivery of the formulation 2.

The carrier 3 or its carrier element or base element 3B is preferably formed from or made up of a composite material of aluminium, polyamide, PVC or sealing lacquer or the like.

The spring portion 4 may be made of the same material or another material. Particularly preferably, the spring portion 4 is made from an elastic plastics, particularly polycarbonate.

According to a particularly preferred aspect which can also be achieved independently, the carrier 3 or the receptacle 3A comprises a particularly or at least substantially angular transition of the edge 3C of the carrier element or base element 3B to the cover 3D, as schematically shown in FIG. 1. This prevents the formation of a sharp angle in this region as otherwise the formulation 2 could be deposited or accumulate there in an undesirable manner. The preferred, at least substantially rectangular transition from the side wall or edge 3C to the cover 3D may in fact counteract such accumulation and/or contributes to an at least substantially complete expulsion of the formulation 2.

Normally, the carrier 3 or its carrier element or base element 3B is produced from a thicker film, a composite material or the like, by hot embossing, blow moulding or thermoforming.

In order to be able to produce the preferably angular or right-angled edge 3C at the transition to the cover 3D, it is preferable to produce it by plastics injection moulding.

It is theoretically possible to deliver several doses and/or different formulations 2 simultaneously—if necessary from different receptacles 3A. The carrier 3 may comprise for this purpose, for example, a plurality of receptacles 3A with optionally different formulations 2. In this case a preferably parallel arrangement of the receptacles 3A is preferred, so that at least substantially identical oscillations or oscillation characteristics are achieved. However, other configurations are also possible.

The dispersing process that is preferably provided (movement of the carrier 3 or the opened or opening receptacle 3A in the air current L for the release and dispersion of the formulation 2 in the air current L) has various advantages. It makes it possible to achieve a very uniform dispersion with good fragmentation of the particles of the preferably powdered formulation 2. It allows a relative independence of the flow rate. In particular, the delivery movement or vibration or oscillation and hence the delivery of the formulation 2 preferably only starts once a flow rate or flow volume of 10 or 20 l/min is achieved. Moreover, an acoustic signal that is perceptible by the user can be produced by the oscillation, i.e., during inhalation.

Other embodiments will be explained in more detail hereinafter with reference to the other Figures. In particular, only essential differences or new aspects will be described in detail. The previous remarks and explanations therefore still apply in a supplementary or corresponding capacity.

FIG. 3 shows a second embodiment of the proposed inhaler 1 in a schematic detailed view similar to FIG. 1.

In the second embodiment the stops 8 and 9 are preferably provided on one side only.

In the second embodiment, apertures, openings or holes 3E located one behind the other in the direction of flow may preferably be produced in the cover 3D. In the second embodiment, the opening device 2 in fact comprises a plurality of piercing elements 7A arranged one after the other in the direction of flow. The opening device 7 is thus preferably designed for producing a plurality of openings or holes 3E. This contributes to a particularly good emptying of the carrier 3 or the receptacle 3A or a good or total expulsion of the formulation 2.

The opening device 7 preferably comprises an actuating element 7B for manual actuation of the opening device 7. In the embodiment shown, the inhaler 1 or the housing 6 preferably comprises a gap 1D through which the actuating element 7B extends outwards. By pressing the actuating element 7B in, the opening device 7 can be actuated and the carrier 3 or the cover 3D can be opened or pierced by means of the piercing elements 7A.

Preferably, the opening device 7 comprises a spring element 7C which resiliently holds the at least one piercing element 7A and the actuating element 7B, particularly in the starting position shown in FIG. 3, from which the piercing elements 7A can be moved into a position that is closer to the carrier 3 (downwards, in FIG. 3), by pressing on the actuating element 7B from outside. After the actuating element 7B has been released, a preferably elastic restoring by the spring element 7C ensures that the starting position is resumed and in particular the gap 1D is closed up again.

However, other design solutions are also possible.

In the second embodiment it is schematically shown that the spring portion 4 is made from a different material or piece of material from the carrier or its carrier element 3A or base element 3B.

The fin 5 may also be made from a different material or piece of material. The fin 5 is then preferably still suitably connected to the carrier or its carrier element or base element 3B.

A third embodiment will now be described with reference to FIGS. 4 and 5. FIG. 4 shows the proposed inhaler 1 in a schematic section corresponding to FIG. 1 with a carrier 3 that is closed off or covered by a covering device 10. FIG. 5 shows the inhaler 1 in a corresponding section but with the covering device 10 removed.

The inhaler 1 according to the third embodiment preferably comprises the covering device 10 for covering the receptacle 3A or its cover 3D. The covering device 10 or a cover element 10A of the covering device 10 can be pulled away or removed from one or more openings or holes 3E of the cover 3D in order to open up the receptacle 3A.

Particularly preferably, the covering device 10 comprises an in particular film-like cover element 10A which covers the carrier 3 or the receptacle 3A or the cover 3D or openings or holes 3E provided in the cover 3D, as schematically shown in FIG. 4. FIG. 4 thus shows the closed state.

The cover element 10A is preferably turned back, flipped over or folded back.

The cover element 10A and/or a grip element 10B of the covering device 10 optionally provided thereon preferably projects out of the inhaler 1 or its housing 6, particularly out of the outlet 1A.

By pulling on the cover element 10A or grip element 10B the cover element 10A can preferably be pulled off or removed. This is particularly easy to do, thanks to the fold-over, as the cover element 10A virtually rolls off when pulled in the region of the bent or folded-over portion and is thus relatively easy to remove or pull away from the carrier 3 or the cover 3D.

The grip element 10B or the cover element 10A preferably has a colour or signal colour that is easy for the user to see, especially red. Accordingly, it is intuitively clear to the user that he has to pull this first of all, i.e., he first has to remove the cover element 10A before he can use the inhaler 1.

Figure 5:
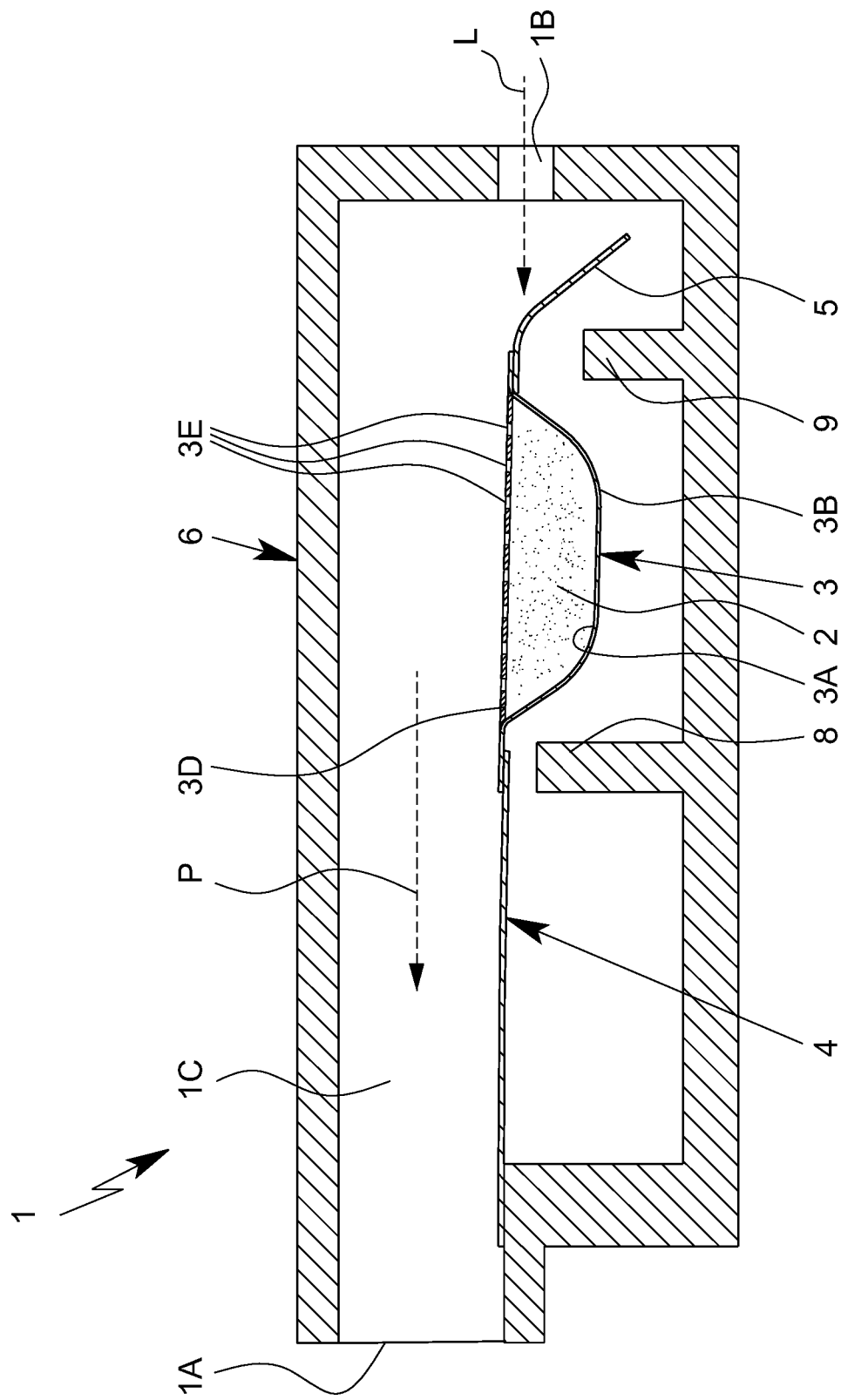

After the detaching of the cover element 10A or removal of the cover element 10A or the covering device 10, the receptacle 3A or the openings or holes 3E are open, as shown in FIG. 5, so that the inhaler can be used directly.

If the cover 3D has only one hole 3E, this is preferably arranged close to the fin 5. If there are two or more holes 3, these are preferably arranged in opposite end regions, viewed in the longitudinal direction or the direction of air flow.

A plurality of holes 3E have the advantage that the blocking of a hole does not have a very serious effect, or has less effect, on the nebulisation or delivery of the formulation 2.

The inhaler 1 or carrier 3 or the cover 3D preferably comprises a plurality of openings or holes 3E, particularly preferably 3 to 5 openings or holes 3E.

The openings or holes 3E are preferably round and/or preferably have a diameter of 0.5 to 3 mm, particularly substantially 1.0 to 2.7 mm, most preferably about 1.5 mm.

The holes 3E do not have to be round but may have any other shape, for example, they may also be triangular, especially to suit the particular opening mechanism or to fit the shape of the receptacle 3A.

The configuration of predetermined or defined openings or holes 3E formed particularly according to the proposal helps to achieve a defined fragmentation and delivery, i.e., nebulisation, of the formulation 2 or the powder particles of the formulation 2.

It should be noted that the cover 3D with the holes 3E may be formed from any material compatible with the active substance, notably, depending on the particular application, from plastics, paper or the like and optionally also from metal or metal foil.

The cover 3D may also be configured as an insert, for example, by a grid-like element or the like inserted in the receptacle 3, and/or may form an assembly with the cover element 10A. Particularly preferably, the cover 3D and the cover element 10A are formed by two superimposed films or layers, the cover 3D in particular containing the perforated structure and the cover element 10A serving as a protection against moisture for the formulation 2 in its unopened state.

The sealing against moisture of the holding chamber or the receptacle 3A for the formulation 2 is then preferably taken over by a cover film, in this case the cover element 10A, in particular.

Alternatively or additionally, however, the entire inhaler 1 may be protected against moisture, for example, by an outer wrapping, foil packaging or the like (not shown).

The inhaler 1 shown is preferably embodied as a disposable inhaler for single use. However, the inhaler 1 may theoretically also be embodied for multiple use (independently of the construction of the cover 3D or independently of the opening by piercing or tearing off). The carrier 3 may then be exchangeable, for example. Alternatively, the inhaler 1 may optionally also contain a number of carriers 3 and/or receptacles 3A, which can be opened individually or independently of one another in order to allow one or more doses of the formulation 2 to be delivered singly or independently of one another.

Individual features and aspects of the different embodiments may also be combined with one another as desired but may also be implemented independently or use in other inhaler designs.

The present invention is not limited to inhalers but may be used in corresponding manner in other nebulisers. Accordingly the term "inhaler" should preferably be understood in a wider sense as encompassing other dispensers or nebulisers, particularly for medicinal or other therapeutic purposes.

LIST OF REFERENCE NUMERALS

1 inhaler
1A outlet
1B inlet
1C flow chamber
1D opening
2 formulation
3 carrier
3A receptacle
3B base element
3C edge
3D cover
3E hole
4 spring portion
4A spring bar
4B slot
5 fin
6 housing
6A lower part
6B upper part
7 opening device
7A piercing element
7B actuating element
7C spring element
8 stop
9 stop
10 covering device
10A cover element
10B grip element
A axis
L air current
P powder current
S oscillation

The invention claimed is:

1. An inhaler (1) for the inhalation of a formulation (2) comprising a carrier (3) in the form of a belt, strip, blister or film, wherein:

at a resting position, the carrier (3) is planar and extends longitudinally along a longitudinal axis, the carrier (3) comprises a free end, an opposing end, and a spring portion (4) located between the free end and the opposing end that is deformable by spring resilience, where the spring portion (4) includes a relatively stiff elastic characteristic that imparts a corresponding relative stiffness in the carrier (3), the carrier (3) includes an oblique fin (5) extending obliquely with respect to the longitudinal axis from the free end of the carrier (3) at least when the carrier is at the resting position, and the opposing end of the carrier (3) is fixed such that air current (L) flowing parallel to the longitudinal axis of the carrier (3) sets the free end of the carrier (3) into motion transversely with respect to the longitudinal axis, and the spring resilience of the spring portion (4) opposes the motion of the free end of the carrier (3) transversely with respect to the longitudinal axis and in combination with continued air current (L) sets the carrier into oscillation (S) by way of a resonance vibration established by the corresponding relative stiffness in the carrier (3) provided by the relatively stiff elastic characteristic of the spring portion (4).

2. The inhaler (1) according to claim 1, wherein the spring portion (4) comprises two spring bars (4A) extending parallel to one another and parallel to the longitudinal axis.

3. The inhaler (1) according to claim 1, characterized in that the spring portion (4) is in the form of a leaf and comprises an opening in the form of a slot or longitudinal slot (4B) extending parallel to the longitudinal axis.

4. The inhaler (1) according to claim 1, characterized in that the spring portion (4) extends at least substantially in a main plane of the carrier (3) or in a plane parallel thereto.

5. The inhaler (1) according to claim 1, further comprising:
- a housing (6) having an inlet (1B) at a first end and an outlet (1A) at an opposing, second end, wherein:
- at a resting position, the carrier (3) is planar and extends longitudinally within the housing (6) between the first and second ends of the housing (6) along the longitudinal axis, and
- the opposing end of the carrier (3) is connected to the housing (6) such that air current (L) entering and flowing through the inlet enters the housing (6) parallel to the longitudinal axis of the carrier (3) and impinges on the oblique fin (5) and sets the free end of the carrier (3) into motion transversely with respect to the longitudinal axis.

6. The inhaler (1) according to claim 5, characterized in that the spring portion (4) permits the carrier (3) to be movable at right-angles to the air current (L) but biases the carrier (3) back towards the resting position in the presence of the air current (L).

7. The inhaler (1) according to claim 5, characterized in that the carrier (3) is pivotable or movable about an axis (A) perpendicular to the longitudinal axis and located in a region of the spring portion (4).

8. The inhaler (1) according to claim 5, characterized in that:
- the carrier (3) is impacted by the air current (L) at least substantially only from the free end opposite to the spring portion (4), and/or
- the air current (L) flows along the carrier (3) at least substantially only parallel to a flat side and/or at least substantially only on a flat side of the carrier (3).

9. The inhaler (1) according to claim 5, characterized in that the oblique fin (5) onto which the air current (L) impinges is adjacent to the inlet (1B) of the inhaler (1).

10. The inhaler (1) according to claim 5, characterized in that the inhaler (1) comprises an opening device (7) for opening a holding chamber (3A) containing the formulation.

11. The inhaler (1) according to claim 10, characterized in that the opening device (7) is formed by a manually deformable wall of the housing (6) and/or comprises at least one piercing element (7A) that is resiliently and/or resettingly mounted.

12. The inhaler (1) according to claim 5, characterized in that the inhaler (1) comprises at least one stop (8, 9) for limiting the oscillation (S) of the carrier (3), the at least one stop (8, 9) being formed within the housing (6) of the inhaler (1).

13. The inhaler (1) according to claim 5, characterized in that the carrier (3) comprises a base element (3B) forming a receptacle (3A) for the formulation (2), and a cover (3D) over the receptacle (3A), wherein the cover (3D) is at least partially covered by a covering device (10) which can be manually opened or removed in order to open the carrier (3) or the cover (3D) for the subsequent dispensing of the formulation (2).

14. The inhaler (1) according to claim 13, characterized in that the covering device (10) comprises:

a cover element (10A) having a first end coupled to a first peripheral edge of the base element (3B) closest to the outlet (1A) of the housing (6) and extending toward the inlet (1B) over the cover 3D and the receptacle (3A) past a second opposing edge of the base element (3B) closest to the inlet (1B), a folded-back portion of the cover element (10A) extending from the second opposing edge of the base element (3B) back over the cover element (10A), the cover (3D) and the receptacle (3A) and out through the outlet (1A), and an associated grip element (10B) for pulling the cover element (10A) out through the outlet (1A) and off the cover (3D).

15. The inhaler (1) according to claim 13, characterized in that the cover (3D) comprises a plurality of holes (3E) communicating with the formulation within the receptacle (3A), which holes (3E) are covered by the covering device (10) when the carrier (3) is closed.

16. The inhaler (1) according to claim 5, characterized in that the inhaler (1) is a single-use inhaler with the carrier (3) arranged within the housing (6).

17. The inhaler (1) according to claim 1, further comprising:

a housing (6) having an inlet (1B) at a first end and an outlet (1A) at an opposing, second end; and a mouthpiece at the outlet (1A) of the housing, wherein:

at a resting position, the carrier (3) is planar and extends longitudinally within the housing between the first and second ends of the housing (6) along the longitudinal axis, the carrier (3) comprises a base element (3B) forming a receptacle (3A) for the formulation (2), and a cover (3D) over the receptacle (3A), wherein the cover (3D) includes at least one opening and is at least partially covered by a covering device (10) which can be manually opened or removed in order to open the carrier (3) or the cover (3D) for the subsequent dispensing of the formulation (2), the covering device (10) comprises a cover element (10A) having a first end coupled to a first peripheral edge of the base element (3B) closest to the outlet (1A) of the housing (6) and extending toward the inlet (1B) over the cover 3D and the receptacle (3A) past a second opposing edge of the base element (3B) closest to the inlet (1B), the covering device (10) comprises a folded-back portion of the cover element (10A) extending from the second opposing edge of the base element (3B) back over the cover element (10A), the cover (3D) and the receptacle (3A) and out through the outlet (1A), and the covering device (10) comprises a grip element (10B) that projects out of the mouthpiece and the outlet (1A) for pulling the cover element (10A) off the cover (3D) and out through the outlet (1A) and out through the mouthpiece.

18. The inhaler (1) according to claim 17, characterized in that the cover (3D), which covers the receptacle (3A) containing the formulation (2), comprises, as the at least one opening, three to five holes (3E), which are covered by the covering device (10) when the carrier (3) is closed.

19. The inhaler (1) according to claim 18, characterized in that the holes (3E) are arranged in opposing end regions of the receptacle (3D).

* * * * *